United States Patent [19]

Lonardi et al.

[11] Patent Number: 4,669,502

[45] Date of Patent: Jun. 2, 1987

[54] MOBILE PHASE SELECTOR DEVICE FOR A CHROMATOGRAPHIC APPARATUS

[75] Inventors: Silvano Lonardi, Cadidavid; Fulvio Ottofaro, Verona, both of Italy

[73] Assignee: 501 Glaxo S.p.A., Verona, Italy

[21] Appl. No.: 797,459

[22] Filed: Nov. 13, 1985

[30] Foreign Application Priority Data

Nov. 20, 1984 [IT] Italy ................. 23677 A/84

[51] Int. Cl.$^4$ ............................................ F16K 11/10
[52] U.S. Cl. ........................ 137/624.18; 137/607; 137/893
[58] Field of Search ............ 422/70, 100, 103; 137/606, 607, 889, 893, 624.11, 624.18, 624.2; 73/23.1; 364/497, 509

[56] References Cited

U.S. PATENT DOCUMENTS

| | | | |
|---|---|---|---|
| 2,899,971 | 8/1959 | Munter | 137/889 X |
| 2,954,028 | 9/1960 | Smith | 137/606 X |
| 3,437,098 | 4/1969 | Stark | 137/607 X |
| 3,926,559 | 12/1975 | Stevens | 422/70 X |
| 4,034,774 | 7/1977 | Clymer | 137/624.2 X |
| 4,165,532 | 8/1979 | Kendall | 137/624.2 X |
| 4,387,075 | 6/1983 | Morgart | 422/70 |

Primary Examiner—Alan Cohan
Attorney, Agent, or Firm—Morgan & Finnegan

[57] ABSTRACT

A device for the automatic selection of the mobile phase to be sent to a chromatographic apparatus, particularly HPLC. The reservoirs containing the different fluids are connected to the lateral channels of a single manifold through solenoid valves controlled by the central processing unit (C.P.U.) of the chromatographic apparatus.

6 Claims, 5 Drawing Figures

MOBILE PHASE SELECTOR DEVICE FOR A CHROMATOGRAPHIC APPARATUS

BACKGROUND OF THE INVENTION

The present invention relates to a device for the automatic selection of one of a plurality of fluids forming the mobile phase in a chromatographic analysis apparatus.

It is known that at present the so-called high pressure liquid chromatography (HPLC) is a widely used analytical technique in analysis laboratories.

The instrumentation employed in the HPLC technique, schematically shown in FIG. 2, is represented by a chromatographic column 2 which operates under particular conditions of pressure, ensured by a suitable pump 11 for the passage of the mobile phase 10 (an appropriately selected mixture of solvents).

Generally the column is inserted in a thermostatically controlled system. The sample under examination (a solution thereof) is "injected", possibly by an automatic sampler 16, in the column wherein, through the action of the mobile phase, the various components are separated from one another and from possible impurities. The material eluted from the column is measured by a detector 13, the response of the latter being recorded in the form of peaks. The calculations necessary for determining the individual components are based on the areas or height of these peaks.

The recorder 14 may be replaced by an integrator/computer 15, which directly provides the analytical results.

The evolution of the technique has led to the marketing of instruments which make it possible to operate under automatic conditions. In the most recent arrangements, in fact, the HPLC chromatograph is equipped with an automatic sampler, i.e. with a device capable of performing the operations of injecting, in succession, a series of samples prepared beforehand. As, however, each type of product and thence each type of analysis requires clearly defined and specific instrumental conditions, it follows that the possibility of automation is limited to a series of homogeneous samples.

In practice, however, one is generally faced with the task of having to analyze several series of different samples, each of which requires different operating parameters and, in particular, different mobile phases.

With the most sophisticated devices it is possible to program certain variations of the machine's parameters and, as far as the mobile phase is concerned, it is also possible, starting with (up to 4) different solvents, to obtain mixtures with varying concentration of the solvents themselves, which enables an extension of the automation possibilities, but not to those cases requiring analysis of a large number of different series with, consequently, a large number of qualitatively different mobile phases. Complete automation can therefore be guaranteed even in the most unfavourable conditions, only when it is possible to change a large number of mobile phase automatically.

From U.S. Pat. No. 4,364,263 it is known a chromatographic system of the HPLC type wherein the solvents selector comprises a six-position rotary pneumatic valve for the inlet of six different mobile phases. Each control pulse supplied by the system CPU is converted to a pneumatic impulse capable of operating the valve.

This device has different inconveniences and limitations.

The number of mobile phases which are selectable is limited and depends upon the number of inlets of the valve. Therefore the possible increase of the number of possible phases would require the construction of an appropriate valve. Furthermore the pneumatic operation makes it indispensable an additional supply of compressed gas which brings about increased costs, encumberances and complexities. Lastly, changing from a phase to another implies a flow interruption, to allow the new positioning of the valve, as well as possible inconveniences deriving from moving mechanical parts.

SUMMARY OF THE INVENTION

It is therefore an object of the present invention to provide a device for the selection of the mobile phase which is free of the above noted drawbacks.

In accordance with the present invention, a device is provided for the selection of one of a plurality of fluids, particularly a solvent which forms the mobile phase in a liquid chromatographic apparatus, comprising a plurality of independent inlets, each connected to a fluid reservoir, and an outlet through which the selected fluid is led to the column of the chromatographic apparatus by means of a pump and under the control of a central processing unit, said device comprising:

an elongated manifold, one end of which forms the said outlet, provided with a plurality of lateral channels;

a plurality of solenoid valves, each connected between one of said channels of the manifold and one of said fluid reservoirs; and means for generating signals capable of controlling the opening of one of the solenoid valves in response to a selection signal composed of electric pulses numerically corresponding to one of the solenoid valves.

In accordance to a further aspect of the present invention a manifold of fluids is provided, being formed of an elongated body crossed longitudinally by a main channel. A plurality of lateral channels, inclined to the direction of the flow in said main channel, open therein.

BRIEF DESCRIPTION OF THE DRAWINGS

The invention will now be described in relation to some preferred but not limitative embodiments thereof making reference to the annexed drawings wherein.

DETAILED DESCRIPTION OF THE PREFERRED EMBODIMENT

Figure 1:
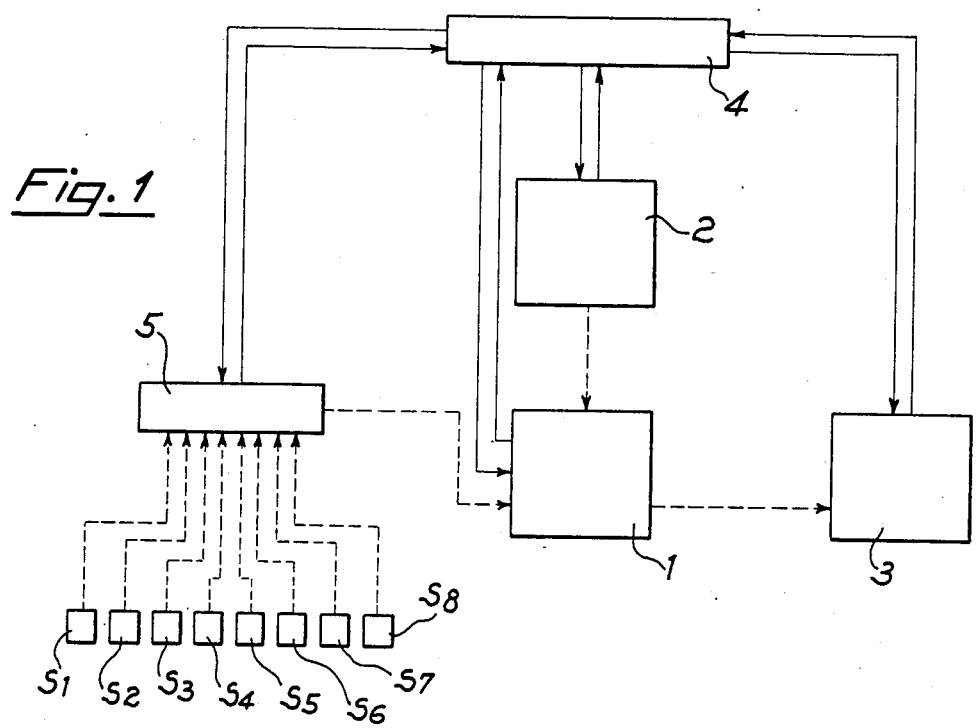
FIG. 1 shows schematically the device of the invention as applied to a HPLC apparatus.
Figure 2:
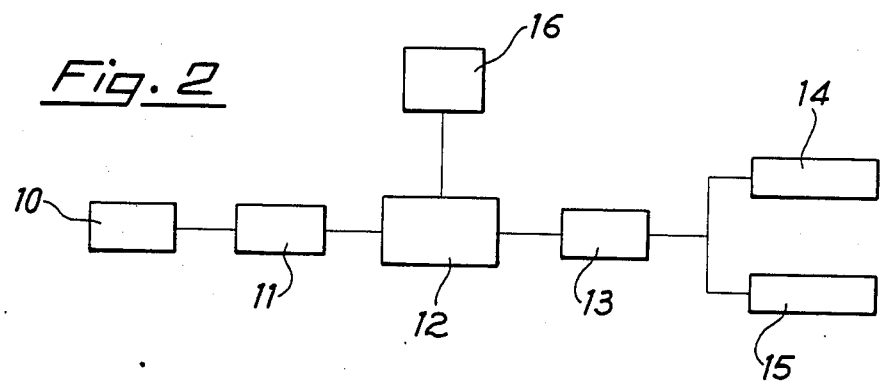
FIG. 2 shows the structure of a known HPLC chromatographic apparatus.

The apparatus schematically shown in FIG. 1 comprises a HPLC chromatograph indicated with the reference number 1, fed by a sampler 2 of the substances to be analyzed, and by a selector 5 of the solvents forming the mobile phases.

The latter are contained in separate reservoirs S1-S8 and therefore the selector represented is capable of selecting among eight possible mobile phases.

Nevertheless it is possible to increase the number of phases in a very simple way, as it will be described later.

The eluted substance from chromatograph 1 is transferred to the detector 3 and the entire system is controlled by a central processing unit 4, preferably consisting of a programmed microprocessor. In FIG. 1, solid lines represent the electrical connections while broken lines schematically indicate movements of fluids. For simplicity sake electrical power supplies have not been shown.

Figure 3:
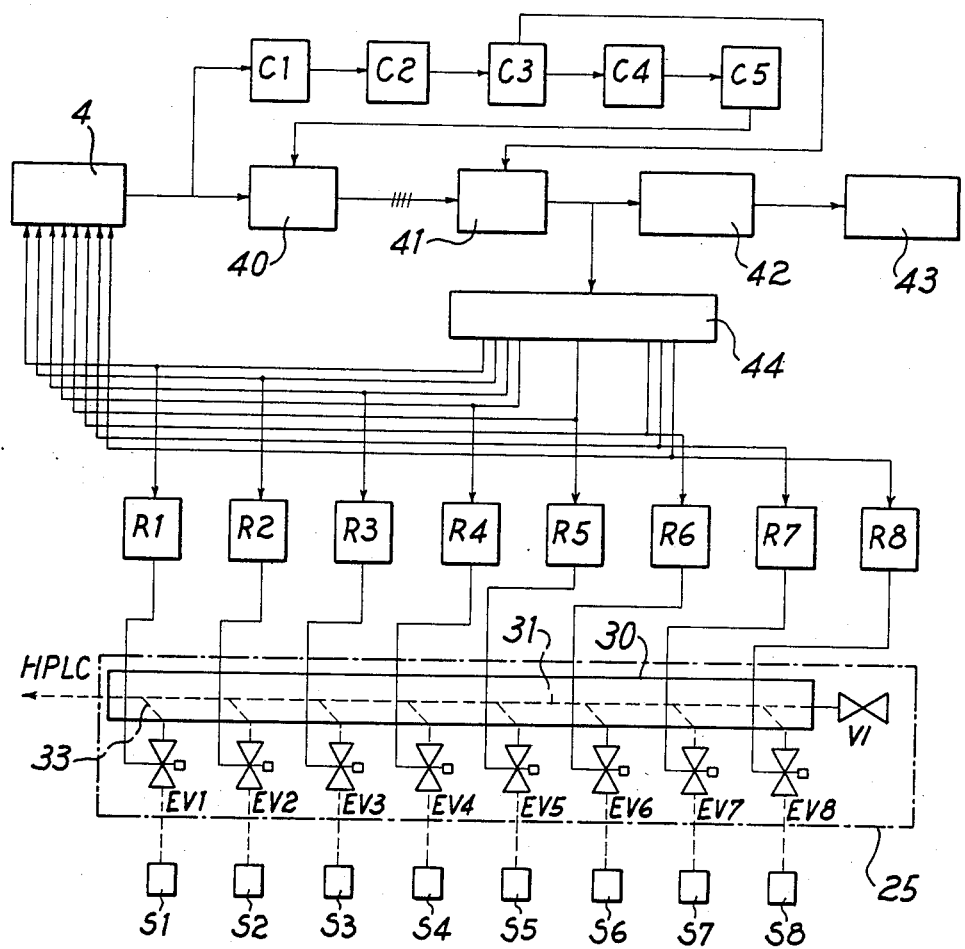
FIG. 3 shows the circuit diagram of the selector according to the invention.

The diagram of selector 5 is shown more in detail in FIG. 3 wherein portion 25 defined by dash-and-dot lines shows the hydraulic portion of the diagram and the remaining portion shows the block diagram of the electronic control portion.

The hydraulic portion 25 of the selector is composed by an elongated manifold 30 having a main channel 31 which crosses it from end to end and a plurality of inlet lateral channels 33, each one connected to a solenoid valve EV1–EV8, which in turn is connected with its respective solvent reservoir S1–S8. Furthermore an auxiliary valve V1 is preferably installed for possible manual operation of the system.

The structure of manifold 30 will be shown more in detail later on with reference to FIG. 5.

Introduction of fluids in the manifold and from this to the HPLC apparatus, takes place automatically and sequentially dependng on the samples which are introduced in the apparatus and it is controlled by the CPU 4 which outputs a sequence of electrical pulses corresponding to the number associated with the desired solvent reservoir.

Preferably a solvent, for example the one contained in S5, is selected with the succession of pulses of equal number, that is 5 pulses, nevertheless it is possible to associate differently the control signals with the reservoirs and in particular to employ redundant and self-checking digital codes.

The pulses supplied by the control unit, after the decoupling by means of transistors (not shown for simplicity sake), are counted by an integrated circuit 40 representing a counter; it collects the serial data and converts it into four output bits.

These four data bits are momentarily stored in the memory 41 in a non-executive mode. At the same time, the first pulse of the succession, besides feeding the counter 40, excites a timer C1 which is part of an enabling circuit formed by five timers C1–C5 connected in cascade.

The first one of these timers, substantially formed by counters fed by a suitable clock, determines, the count time of the counter 40 and it is set for a period of time sufficient to make allowance for any delays in the arrival of the pulses due, for example, to the CPU being occupied and momentarily unavailable.

As soon as such period of time has elapsed, the first timer excites the second which remains activated for a shorter period of time, whereupon it will excite the third timer C3.

The timer C2 does not exert any action on the subsequent circuits, but merely serves for decoupling the counting function controlled by C1 and the function of enabling the memory which is controlled by C3. Thus C3 has the function of enabling the memory 41, which contains, in a latent state, the four data bits corresponding to the number that the counter has received from the CPU.

A logic level "1", lasting approximately 1 second, activates the memory and transfers the four bits in parallel mode to the display driver circuit 42 and to the demultiplexer 44. The display drive circuit decodes the four data bits into output signals which, by a common emitter transistor matrix system (not shown), feed the segments of a display 43.

Demultiplexer 44 decodes the four bits and opens one of the sixteen logic switches, 0 to 15, contained therein. Demultiplexer 44 operates at logical level "0", i.e. all output pins, 0 to 15, are at high logic level and switch to low logic level when they are activated.

Figure 4:
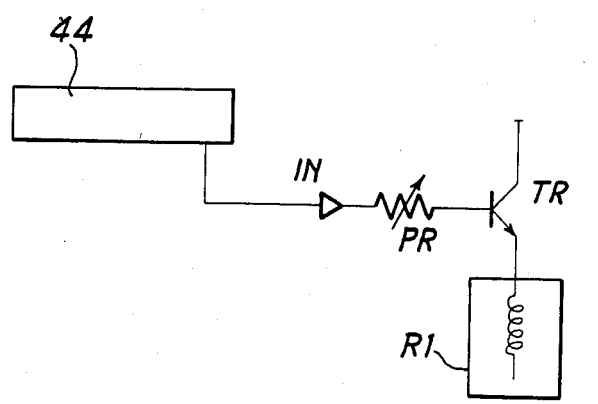
FIG. 4 shows a power adaptor circuit.

The signal which is obtained from each switch is inverted in its logic configuration by inverters IN so as to obtain a signal of approximately +5 V, as shown in the detail of FIG. 4, relative to a single one of the lines.

These signals are picked up by the bases of a common collector transistor matrix, the emitters of which through their respective collector close eight circuits which in turn feed the bases of eight medium power transistors which supply +5 V to the coils of eight relays. An example of one of these circuits is shown in FIG. 4.

With reference to FIG. 4, before the input nodes to each of the bases of the eight medium power transistors, a multirev. trimmer PR has been inserted for the fine adjustement of the exciting current to the coils. This is highly preferred because the relay coils have different resistances and thus, in case of replacement, it will be necessary to slightly adjust the exciting current. Each of the eight relays closes an auxiliary power supply circuit at a stabilized voltage of +24 V d.c., which energizes the corresponding solenoid valve.

After the excitation period has elapsed, C3 activates the fourth timer C4 which remains operative for a certain period of time, after which it excites the fifth timer C5 which, with a pulse at logic level "1", resets the counter 40 thus preparing the entire system for the next counting operation. The full cycle is controlled by the five timers in cascade, and the total time of execution is of few seconds.

It should be stressed that the valve selection system is subject to a rigid feed back control. The logic output signal from each channel of the demultiplexer, besides closing the corresponding relay by means of the respective excitation circuit, is transmitted to the CPU for checking; if the condition is different from the preset condition, the CPU attempts to restore the required conditions. If after a predetermined number of attempts, the situation is still not the one required, the CPU switches off the entire system.

The solvent, filtered through a porous diaphragm (for example a 10 μm diaphragm), located on the fluid line inside the reservoir, reaches the inlet of the corresponding valve. The solenoid valves EV1–EV8 are of the normally closed type. Under the control of the electronic circuit, one of the eight relays actuates the corresponding solenoid valve, causing the required solvent to pass through the manifold. The switching over from one solenoid valve to another is instantaneous and not sequential.

Figure 5:
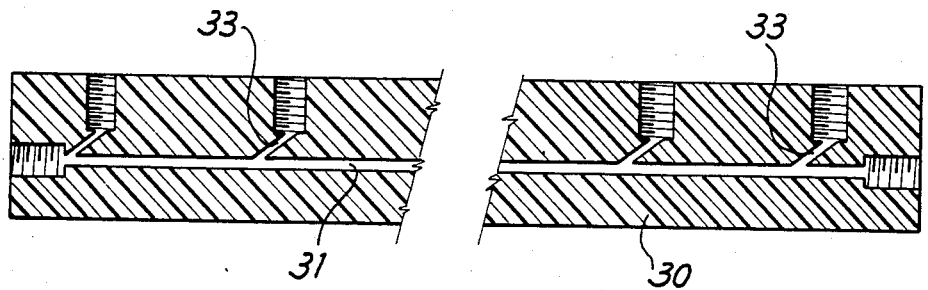
FIG. 5 shows a manifold in accordance with the invention.

The manifold 30 shown in FIG. 5 consists of an elongated parallelepiped block of an inert material, for example polytetrafluoroethylene, longitudinally crossed by a main channel 31 having a circular cross-section which is intersected, at an angle preferably comprised between 40° and 50°, by eight lateral channels 33, all having the same diameter. Such an inclination, in the direction of the flow, makes it possible to reduce turbolent motions of the solvent under the suction action of the pump.

From the foregoing, the advantages afforded by the present invention should be clear. In fact conversions from electrical signals to pneumatic impules are no longer required, thus obviating the necessity of a suitable feed line for compressed gas and reducing the number of components (many of which movable).

Furthermore, by virtue of the special manifold used, the prior limitations as to the number of usable phases and of constructional character are overcome. The number of reservoirs may, in fact, be considerably increased, as it is sufficient to increase the length of the manifold member and, if it is the case, to modify the control logics.

Lastly, switching over from a phase to another takes place without interruption of the flow and it is thus possible to operate continuously the pump.

Though the invention has been described with particular reference to some preferred embodiments, it is not limited thereto but it extends to trivial variations and/or modifications which will be easily recognized by those skilled in the art.

What we claim is:

1. A device for the selection of one of a plurality of fluids, particularly a solvent forming the mobile phase in a liquid chromatographic apparatus, said device comprising a plurality of independent inlets, each one connected to a fluid reservoir, and an outlet through which the selected fluid is introduced in the column of the chromatographic apparatus through a pump and under control of a central processing unit, said device comprising:

an elongated manifold, one end of which forms said outlet, and provided with a plurality of lateral channels;

a plurality of solenoid valves, each one connected between one of said channels of the manifold and one of said fluid reservoirs;

means to generate signals capable of controlling the opening of one of the solenoid valves in response to a selection signal formed by electrical pulses numerically corresponding to one of the solenoid valves;

a counter of the selection pulses relating to the selected valve, connected to the central processing unit through a data line;

a memory connected to the counter output for temporarily storing the selection data;

a demultiplexer connected to the output of the memory and having a number of outputs at least equal to the number of the solenoid valves to be controlled;

a plurality of relays, each of them connected to one of said outputs of the demultiplexer, each relay operating the corresponding solenoid valve in response to an activation signal at the corresponding output of the demultiplexer; and an enabling circuit having its input connected to the data line and the outputs to the memory and to the counter, respectively, which outputs control the enabling of the memory for the transfer of the selection data to the demultiplexer and, respectively, the subsequent reset of the counter before starting of a new cycle of selection.

2. A device according to claim 1, wherein said enabling circuit comprises a chain of timers actuated by the arrival of the first pulse of the succession of pulses, which provides the selection signal for a solenoid valve.

3. A device according to claim 1, wherein the outputs of the demultiplexer are brought back to the central processing unit for comparison with the selection data originally produced by the central processing unit.

4. A device according to claim 1 wherein said manifold is formed of an elongated body longitudinally crossed by a main channel in which open a plurality of lateral channels, inclined at an angle with respect to the direction of flow in said main channel, the inlets of which are controlled by solenoid valves.

5. A device according to claim 4, wherein said manifold lateral channels have a circular cross-section of identical and constant diameter. and 6. A device according to claim 5, wherein said manifold lateral channels have parallel axes inclined by an angle comprised between 40° and 50° with respect to the axis of the main channel.

* * * * *

UNITED STATES PATENT AND TRADEMARK OFFICE
CERTIFICATE OF CORRECTION

PATENT NO. : 4,669,502

DATED : June 2, 1987

INVENTOR(S) : Silvano Lonardi et al.

It is certified that error appears in the above-identified patent and that said Letters Patent is hereby corrected as shown below: Title Page:

Patent Cover page, item [73] Assignee, delete "501".

Signed and Sealed this

Eighth Day of March, 1988

*Attest:*

DONALD J. QUIGG

*Attesting Officer*  *Commissioner of Patents and Trademarks*